United States Patent
Saji et al.

(10) Patent No.: US 9,044,520 B2
(45) Date of Patent: Jun. 2, 2015

(54) COMPOUND ACCUMULATING IN INFLAMMATORY SITE, DIAGNOSTIC AGENT CONTAINING THE COMPOUND IN LABELED STATE AND ITS PRECURSOR COMPOUND FOR LABELING

(75) Inventors: Hideo Saji, Kyoto (JP); Hiroyuki Kimura, Kyoto (JP); Masahiro Ono, Kyoto (JP); Ikuya Seki, Tokyo (JP)

(73) Assignees: Nihon Medi-Physics Co., Ltd., Tokyo (JP); Kyoto University, Kyoto (JP)

( * ) Notice: Subject to any disclaimer, the term of this patent is extended or adjusted under 35 U.S.C. 154(b) by 480 days.

(21) Appl. No.: 13/434,722

(22) Filed: Mar. 29, 2012

(65) Prior Publication Data
US 2012/0253010 A1 Oct. 4, 2012

(30) Foreign Application Priority Data
Mar. 30, 2011 (JP) .................. 2011-090476

(51) Int. Cl.
A61K 51/00 (2006.01)
A61M 36/14 (2006.01)
A61K 51/08 (2006.01)

(52) U.S. Cl.
CPC ........ A61K 51/088 (2013.01); G01N 2800/042 (2013.01)

(58) Field of Classification Search
CPC ..... A61K 51/08; A61K 51/088; A61K 51/00; A61K 51/04; A61K 51/06; A61K 2121/00; A61K 2123/00; A61K 38/00; A61K 38/03; A61K 38/07; A61K 38/08; C07K 7/06; C07K 7/00; C07K 2/00; C07K 4/00; C07K 14/00; C07K 5/00; C07K 5/10; G01N 2800/042
USPC ............ 424/1.1, 1.65, 1.69, 9.1, 9.2, 9.3, 9.4, 424/9.5, 9.6; 514/1, 1.1; 530/300, 324, 325, 530/326, 327, 328, 329, 330
See application file for complete search history.

(56) References Cited

U.S. PATENT DOCUMENTS

| | | | |
|---|---|---|---|
| 4,986,979 A | 1/1991 | Morgan | |
| 5,792,444 A | 8/1998 | Fischman et al. | |
| 2006/0057064 A1 | 3/2006 | Seki et al. | |

FOREIGN PATENT DOCUMENTS

| | | |
|---|---|---|
| JP | 2931093 | 5/1999 |
| WO | WO 2009/9013317 | 11/1990 |
| WO | WO 2004/029080 A1 | 4/2004 |

OTHER PUBLICATIONS

Verbeke et al, Nuclear Medicine and Biology, 2000, vol. 27, pp. 769-779.*
Niedel et al, The Journal of Biological Chemistry, 1979, vol. 254, No. 21, pp. 10700-10706.*
Baidoo et al, High-Affinity No-Carrier-Added 99m Tc-Labeled Chemotactic Peptides for Studies of Inflammation in Vivo, Bioconjugate Chemistry, Mar.-Apr. 1998, 9(2), 208-217.
Day et al, Synthesis and Binding Characteristics of an Intrinsically Radiolabeled Chemotactic Acy L Tripeptide, FEBS Letters, May 1977, 77(2), 291-294.
Jiang et al, Localization of Abscess with an Iodinated Synthetic Chemotactic Peptide, Nuclear Medicine, Jun. 1982, 21(3),110-113.
Verbeke et al, Influence of the Bifunctional Chelate on the Biological Behavior of 99m Tc-Labeled Chemotactic Peptide Conjugates, Nuclear Medicine & Biology, Nov. 2000, 27(8), 769-779.

* cited by examiner

*Primary Examiner* — D. L. Jones
(74) *Attorney, Agent, or Firm* — Baker & Hostetler LLP

(57) ABSTRACT

Embodiments of the invention provide a compound accumulating in an inflammatory site, a diagnostic agent containing the compound in labeled state and its precursor compound for labeling. Such a compound accumulating in inflammatory site may be represented by the following formula (1):

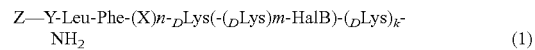

$$Z-Y\text{-Leu-Phe-}(X)n\text{-}_DLys(-(_DLys)m\text{-HalB})\text{-}(_DLys)_k\text{-}NH_2 \quad (1)$$

wherein
in the formula (1),
Z represents a protective group for an amino group;
Y represents Met or Nle;
X represents a spacer consisting of one or more of amino acid and/or synthetic organic compounds;
n represents 1 or 0;
m represents 1 or 0;
k represents 1 or 0; and
HalB represents a substituted benzoic acid having a radioactive halogen in an aromatic ring.

17 Claims, 2 Drawing Sheets

PET Images of Example 3

Axial      Coronal      Sagittal

PET Images of Example 4

Axial      Coronal      Sagittal

PET images of Example 5

Axial      Coronal      Sagittal

COMPOUND ACCUMULATING IN INFLAMMATORY SITE, DIAGNOSTIC AGENT CONTAINING THE COMPOUND IN LABELED STATE AND ITS PRECURSOR COMPOUND FOR LABELING

CROSS REFERENCE TO RELATED APPLICATIONS

This application claims priority to Japanese Patent Application No. JPA2011-90476, filed on Mar. 30, 2011, the contents of which is incorporated by reference herein in its entirety.

TECHNICAL FIELD

The present invention relates to a compound accumulating in inflammatory site, a diagnostic agent containing the compound in labeled state and its precursor compound for labeling. More in detail, the present invention relates to a novel compound having radioactive halogen and properties of accumulation specific to the inflammatory site in vivo in association with a seat of disease including diabetic foot. Also the present invention relates to a diagnostic agent containing said compound in labeled state as the active ingredient which is useful for Nuclear Medicine Diagnosis and its precursor compound for labeling.

BACKGROUND

The present invention relates to a compound accumulating in inflammatory site, a diagnostic agent containing the compound in labeled state and its precursor compound for labeling. More in detail, the present invention relates to a novel compound having radioactive halogen and properties of accumulation specific to the inflammatory site in vivo in association with a seat of disease including diabetic foot. Also the present invention relates to a diagnostic agent containing said compound in labeled state as the active ingredient which is useful for Nuclear Medicine Diagnosis and its precursor compound for labeling.

Animals including humans bring protecting systems defined as immune response when, for example, subjected to harmful external stimuli. Inflammation reaction is a phenomenon appeared as a part of results of the immune response such as removal of extraneous substances infiltrated into an individual, demolition of invaded tissue and restoration of injured tissue.

A typical phenomenon of such inflammation reaction is also induced in a diabetic foot. A diabetic foot is an ulcer or a destructive lesion of deep tissues caused mainly by an infection, occurring in the lower extremity of a diabetic patient, and is a lesion complicated by neuropathy and various degrees of peripheral blood flow disturbance. The progression of the diabetic foot results in significant consequences in which necrosis occurs in the tissue of the lesion site and the foot needs to be amputated. Thus, it is necessary to detect a diabetic foot early for treatment and to perform an effective treatment while monitoring the efficacy of the treatment.

Leukocytes are included as one of important factors in the inflammation reaction and chemotactic formylated peptides considered to bind to leukocytes through the formylated peptide receptor (hereinafter designated as FPR).

A peptide containing formyl-methionyl-leucyl-phenylalanyl (fMLF), which is a chemotactic formylated peptide, is known as a peptide having affinity for FPR. Also, accumulation of fMLF labeled with a radioactive nuclide is observed in acute inflammation with neutrophils infiltration. Day, A R. et al., FEBS Lett. 77, 291-294 (1977) describes fMLF labeled with the radionuclide $^{125}$I. Jiang, M S. et al., Nuklearmedizin, 21, 110-113 (1982) describes that fMLF labeled with the radionuclide $^{125}$I accumulates in inflammation in the body. Japanese Patent No. 2931093 discloses $^{111}$In fMLF mediated by DTPA (diethylenetriamine pentaacetic acid). Verbeke, K. et al., Nuclear Medicine & Biology, 27, 769-779 (2000) describes Tc-99m fMLF mediated by mercaptoacetylglycylglycine. Baidoo, K. E. et al., Bioconjugate Chemistry, 9, 208-217 (1998) describes Tc-99m fMLF mediated by a diaminodithiol compound. U.S. Pat. No. 4,986,979 describes the use of radionuclide-containing fMLF for in vitro labeling of white blood cells with the radionuclide via the photoaffinity thereof. U.S. Pat. No. 5,792,444 describes fMLF capable of being labeled with a radionuclide. International Publication No. WO 2004/029080 discloses a peptide containing a site for binding to the receptor FPR of white blood cells, a site for enhancing the binding thereof to monocytes and lymphocytes in all white blood cells, and a site capable of being labeled with a radioactive metal.

SUMMARY

There is further a need for a radiolabeled peptide having the optimum structure for performing diagnostic imaging of inflammatory site induced in a diabetic foot including SPECT and PET, and in order to use the said radiolabeled peptide further as a active ingredient in a diagnostic agent, it desirably has sufficiently higher affinity for FPR expressed on leukocytes as a target, that is, higher accumulation in the inflammatory site thereon, than for fMLF found in nature. However, no prior art has found a radioactive compound sufficiently satisfying the requirement.

In such situations, an object of the present invention is to provide a compound accumulating in inflammatory site in vivo in association with a seat of disease including a diabetic foot, and that is capable to be labeled with a radioactive halogen, a diagnostic agent contained said compound in labeled state as the active ingredient which is useful for SPECT and PET image diagnosis, and its precursor for radiolabeling.

A first aspect of the present invention relates to a compound that accumulate in inflammatory site represented by the following formula (1):

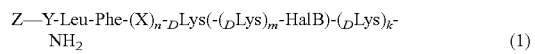

wherein, in the formula (1),

Z represents a protective group for an amino group;

Y represents Met or Nle;

X represents a spacer consisting of one or more of amino acid and/or synthetic organic compounds;

n represents 1 or 0;

m represents 1 or 0;

k represents 1 or 0; and

HalB represents a substituted benzoic acid having a radioactive halogen in its aromatic ring.

A second aspect of the present invention relates to a diagnostic agent for imaging an inflammatory site by the above formula (1) in a labeled state with radioactive halogen as the active ingredient.

Furthermore, a third aspect of the present invention relates to a precursor compound for radioactive halogen compounds of the first aspect, represented by the following formula (2):

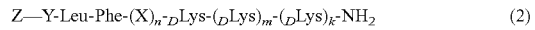

wherein, in the formula (2),
Z represents a protective group for an amino group;
Y represents Met or Nle;
X represents a spacer consisting of one or more of amino acid and/or synthetic organic compounds;
n represents 1 or 0;
m represents 1 or 0; and
k represents 1 or 0.

Embodiments of the present invention provide a compound accumulating in an inflammatory site in vivo in association with a seat of disease, including a diabetic foot, that is capable of being labeled with a radioactive halogen, a diagnostic agent contained said compound in a labeled state as the active ingredient which is useful for SPECT (single-photon emission computed tomography) and PET (positron image tomography) image diagnosis, and its precursor for radiolabeling.

DETAILED DESCRIPTION OF ILLUSTRATIVE EMBODIMENTS

Figure 1:
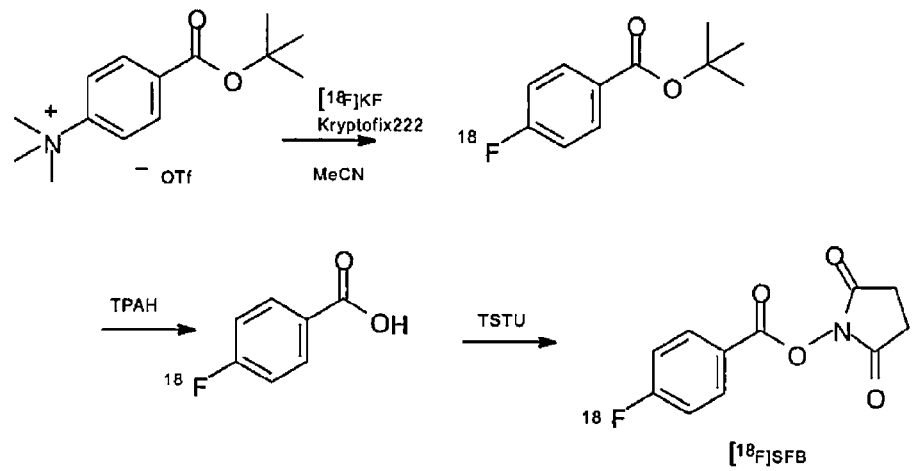
FIG. 1 shows a synthetic scheme for a radioactive halogen-containing monomer, [$^{18}$F]SFB.

Embodiments of the present invention will be described below in detail.

Amino acids used herein are represented by their three characters expression, and unless otherwise noted, the left hand of it shows the N-terminal side and the right hand of it shows the C-terminal side. In this respect, Nle represents norleucine. Unless otherwise noted, inside of the parentheses following an amino acid indicates a peptide or an organic compound bound to the side chain thereof. In addition, in the amino acid sequence enclosed in parentheses, the right side is indicated as the N-terminal side, and the left side as the C-terminal side to facilitate the understanding of the entire structure thereof. Furthermore, in the present specification, an amino acid with D-configuration is designated as $_D$amino acid.

The compound accumulating in an inflammatory site of embodiments of the present invention is represented by the following formula (1):

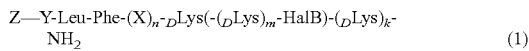

In the formula (1), Z represents a protective group for an amino group including, for example, acyl group with 1 to 9 carbon atoms such as formyl group or acetyl group, acyloxy group with 2 to 9 carbon atoms such as t-Boc group (tert-butoxycarbonyl group), a lower alkyl group with 1 to 6 carbon atoms such as methyl, ethyl, and propyl groups, and carbamyl group. Among these, a formyl group may be preferred in view of affinity for FPR.

In the formula (1), Y represents Met or Nle as an amino acid.

In (X)$_n$ of the formula (1), X represents a spacer consisting of at least one amino acid and/or compound capable of an organic synthesis and n represents 0 or 1. In embodiments, it may be preferred that X is (-Nle-Tyr-) and n is 1.

In the formula (1), m represents 0 or 1.

In the formula (1), HalB represents substituted benzoic acid having radioactive halogen in its aromatic ring. Examples of radioactive halogens in HalB include $^{121}$I, $^{123}$I, $^{125}$I, and $^{131}$I for use in SPECT and can include $^{124}$I and $^{18}$F for use in PET. $^{18}$F (HalB in this case is represented by "[$^{18}$F]FB") may be preferable for use in PET in view of its versatility. In this respect, FB represents fluorobenzoyl group.

More specifically, the following compounds binding to leukocytes may be exemplified as preferred embodiments:
Formyl-Met-Leu-Phe-Nle-Tyr-$_D$Lys-ϵ([$^{18}$F]FB)-NH$_2$;
Formyl-Met-Leu-Phe-Nle-Tyr-$_D$Lys-$_D$Lys-ϵ([$^{18}$F]FB)-NH$_2$;
Formyl-Nle-Leu-Phe-Nle-Tyr-$_D$Lys-ϵ([$^{18}$F]FB)-NH$_2$;
Formyl-Nle-Leu-Phe-Nle-Tyr-$_D$Lys-$_D$Lys-ϵ([$^{18}$F]FB)-NH$_2$;
Formyl-Nle-Leu-Phe-Nle-Tyr-$_D$Lys-ϵ([$^{18}$F]FB)-$_D$Lys-NH$_2$; and
Formyl-Met-Leu-Phe-Nle-Tyr-$_D$Lys-ϵ([$^{18}$F]FB)-$_D$Lys-NH$_2$.

The compound that accumulates in an inflammatory site of the present invention can be synthesized, for example, according to the method using steps 1 to 3 as described below.

[Step 1] Synthesis of Precursor Compound

The peptide as the precursor can be prepared by a peptide synthesis method known as a "solid-phase method" or a "liquid-phase method." The peptide synthesis is described in detail, for example, in Seikagaku Jikken Koza (Lecture on Biochemical Experiments), ed. the Japanese Biochemical Society, Vol. 1, "Tanpakushitsu (Protein) IV," pp. 207-495 (1977), published by Tokyo Kagaku Dojin and Shin Seikagaku Jikken Koza (New Lecture on Biochemical Experiments), ed. the Japanese Biochemical Society, Vol. 1, "Tanpakushitsu (Protein) VI," pp. 3-74 (1992), published by Tokyo Kagaku Dojin. It can also be synthesized by the Fmoc (9-fluorenylmethoxycarbonyl) solid-phase synthesis method using a peptide synthesizer. That is, a peptide of interest can be synthesized by binding an Fmoc amino acid into which an amino acid corresponding to the C-terminus of each peptide to be synthesized is introduced into a resin, repeating the operation of (I) the deprotection and washing of the Fmoc group and (II) the condensation and washing of an Fmoc amino acid to extend the peptide chain, and finally performing a final deprotection reaction.

The isolation and purification of the peptide can be performed by combining known separation operations. For example, a method for purifying a peptide or a protein may be used such as ion-exchange chromatography, hydrophobic chromatography, reverse phase chromatography, or high-performance liquid chromatography, and these methods may be properly combined, if necessary. According to a final type of usage, the purified peptide may be concentrated, and if necessary further lyophilized, for isolation.

[Step 2] Synthesis of Radioactive halogen-Containing Monomer [$^{18}$F]SFB

The radioactive halogen-containing monomer [$^{18}$F]SFB can be obtained according to procedures as described below (FIG. 1). SFB represents N-succinimidyl-4-fluorobenzoic acid, and [$^{18}$F]SFB represents N-succinimidyl-4-[$^{18}$F]fluorobenzoic acid.

1. A phase-transfer catalyst is dissolved in dehydrated acetonitrile in a light-shielded vial (hereinafter referred to as a "reaction vial"), to which a K$_2$CO$_3$ aqueous solution of $^8$F— is then added in an amount corresponding to a necessary radioactivity before stirring. As the phase-transfer catalyst, various compounds having the property of forming an inclusion complex with an $^{18}F$ ion may be used. Specifically, various compounds used for producing radioactive fluorine-labeled organic compounds may be used; 18-crown-6-ether and other various aminopolyethers may be used. In embodiments, Kryptofix 222 (trade name, manufactured by Merck Ltd.) may be used preferentially.

2. The reaction vial is heated while blowing nitrogen gas thereinto until the solvent evaporates. In addition, the solvent including water is completely driven off by the repeat of adding dehydrated acetonitrile and evaporating of it several times.

3. t-Butyl 4-N,N,N-trimethyl-ammoniumbenzoate triflate is dissolved in dehydrated acetonitrile, which is then added to the reaction vial before vigorously stirring for reaction. The quantitative ratio of t-butyl 4-N,N,N-trimethyl-ammoniumbenzoate triflate to dehydrated acetonitrile is not limited as long as t-butyl 4-N,N,N-trimethyl-ammoniumbenzoate triflate is completely dissolved; however, preferably, when the amount of t-butyl 4-N,N,N-trimethyl-ammoniumbenzoate triflate is 0.3 to 0.5 mg, the amount of dehydrated acetonitrile may be 100 to 200 μL.

4. After reaction, tetrapropylammonium hydroxide is added to the reaction vial before stirring for reaction.

5. After reaction, TSTU is dissolved in (dehydrated) acetonitrile, which is then added to the reaction vial before stirring for reaction.

6. The reaction solution in the reaction vial is diluted with a 5% acetic acid aqueous solution, and is then passed through Sep-Pak (trademark, manufactured by Nihon Waters K.K.) plus PS-2 activated with acetonitrile and water; the column is washed with water/acetonitrile and the radiohalogen-containing monomer $[^{18}F]SFB$ is eluted using acetonitrile.

Figure 2:
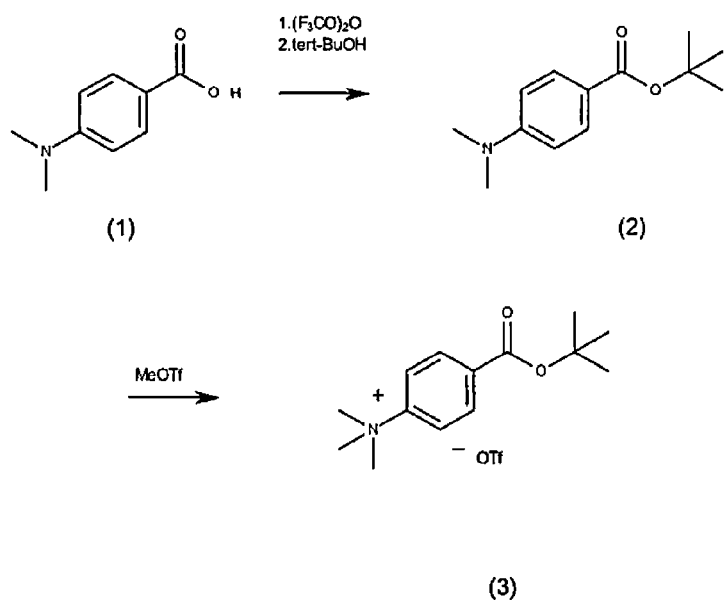
FIG. 2 shows a synthetic scheme for t-butyl 4-N,N,N-trimethyl-ammoniumbenzoate triflate.

A method is known for producing t-butyl 4-N,N,N-trimethyl-ammoniumbenzoate triflate as the starting material in the above method (for example, Applied Radiation and Isotopes 59 (2003) 43-48), which can be synthesized according to the following procedures (FIG. 2).

Trifluoroacetic anhydride is added to cooled dry THF containing 4-N,N-dimethylamino benzoic acid ((1) in FIG. 2). Some time later (e.g., after 30 minutes), tert-BuOH is added thereto, which is then kept at room temperature (e.g., for 2 hours). Thereafter, the resulting mixture is poured into a saturated NaHCO$_3$ aqueous solution, which is then extracted with CH$_2$Cl$_2$. The extract is passed through a short silica gel column and the solvent is removed under reduced pressure to provide tert-butyl ester ((2) in FIG. 2).

The above tert-butyl ester is dissolved in nitromethane, which is then cooled. Methyl triflate is added thereto, which is then stirred (e.g., for 1 hour). The reaction product is poured into diethyl ether, which is then vacuum dried to provide t-butyl 4-N,N,N-trimethyl-ammoniumbenzoate triflate ((3) in FIG. 2).

[Step 3] Labeling of Peptide

The peptide as the precursor for the radiolabeling is dissolved in a mixture of acetonitrile (MeCN) and a borate buffer, which is then added to $[^{18}F]SFB$ concentrated in a stream of Ar at 70° C. The resulting mixture is adjusted to a pH of 8.5 to 9.0 with MeCN/triethylamine (hereinafter denoted by Et$_3$N)=98/2 for reaction. After reaction, the deprotection reaction of Fmoc is performed. Piperidine is added thereto to make a solution having a concentration of 20%, which is then reacted for 15 to 30 minutes. Separation and purification are performed using HPLC, followed by purity determination.

The compound of the present invention may have a high accumulation in inflammatory sites and can be optimally used as a main ingredient of a nuclear medicine imaging agent including diagnosis of an inflamed site associated with a diabetic foot. Examples of diseases accompanied by an inflammation can include a diabetic foot and inflammatory bowel disease.

The agent for radioisotope diagnosis containing the compound of the present invention may be prepared as a solution in which a radioactive iodine-labeled peptide according to embodiments of the present invention is dissolved. As the liquid for dissolving the radioactive iodine-labeled peptide, water, saline, Ringer's solution, or the like may be used. When the radioactive iodine-labeled peptide has low water solubility, a solubilizer may be added to the peptide or the peptide may be dissolved in a liquid capable of dissolving the peptide and then the resulting liquid may be mixed with a biologically tolerable liquid, if necessary. For example, a method may be used which involves dissolving the peptide in DMSO and adding a binding buffer or saline thereto so as to provide 10% DMSO to prepare an aqueous solution. A stabilizer may also be blended, if necessary.

The dosage of the diagnostic agent containing the compound of the present invention does not need to be particularly limited if the concentration of the agent administered is sufficient to image the distribution thereof. For example, the $^{18}F$-labeled peptide may be used by intravenous or local administration in an amount of about 50 to 600 MBq per adult having a body weight of 60 kg. The distribution of the agent administered can be imaged by a known method using a PET apparatus or a SPECT apparatus.

EXAMPLES

The present invention is described in more detail using examples, but the scope of the present invention should not be limited thereto.

Non-radioactive form of peptides of the present invention and the control peptide are described below in Example 1 and 2.

Non-radioactive form of peptides of the present invention

Peptide 1: formyl-Met-Leu-Phe-Nle-Tyr-$_D$Lys-ϵ([$^{19}$F]FB)-NH$_2$

Peptide 2: formyl-Nle-Leu-Phe-Nle-Tyr-$_D$Lys-ϵ([$^{19}$F]FB)-NH$_2$

Peptide 3: formyl-Met-Leu-Phe-Nle-Tyr-$_D$Lys-$_D$Lys-ϵ([$^{19}$F]FB)-NH$_2$;

Peptide 4: formyl-Nle-Leu-Phe-Nle-Tyr-$_D$Lys-$_D$Lys-ϵ([$^{19}$F]FB)-NH$_2$

Peptide 5: formyl-Met-Leu-Phe-Nle-Tyr-$_D$Lys-ϵ([$^{19}$F]FB)-$_D$Lys-NH$_2$

Control Peptides

Peptide 6: formyl-Nle-Leu-Phe-Nle-Tyr-$_D$Lys-$_D$Lys-$_D$Lys-ϵ([$^{19}$F]FB)-NH$_2$ Peptide 7: formyl-Nle-Leu-Phe-Nle-Tyr-$_D$Lys-$_D$Lys-$_D$Lys-$_D$Lys-ϵ([$^{19}$F]FB)-$_D$Lys-NH$_2$ Using an automated peptide synthesizer (Model 433A, manufactured by Applied Biosystems, Inc.), peptides were each synthesized by a method which involves binding amino acids one by one to an amino acid derivative immobilized on a resin from the carboxyl terminal sides thereof (a solid-phase synthesis method).

In the synthesis of a compound labeled with non-radioactive fluorine, an amino acid having non-radioactive FB introduced into the side chain of lysine according to a known method was prepared in advance and used as a raw material for synthesis using the automated synthesizer.

The amino acid having non-radioactive FB (hereinafter referred to as "[$^{19}$F]FB") introduced into the side chain of lysine was prepared as follows. Specifically, Fmoc-Lys (5 g, 13.6 mmol) was dissolved in water:THF (1:9, 30 ml), to which DIEA (4.7 ml, 27.1 mmol, diisopropylethylamine) was then added, followed by adding FB-Cl (1.53 ml, 12.9 mmol, 4-F-benzoic acid chloride) thereto with stirring under ice cooling. Thereafter, the reaction solution was stirred a whole day and night, and then added to a 0.5 mol/L hydrochloric acid aqueous solution (300 ml), followed by extracting the title derivative of interest with 300 ml of ethyl acetate. The resulting ethyl acetate layer was dried with sodium sulfate and concentrated under reduced pressure to provide a white solid powder. This was used as an amino acid derivative raw material for the appropriate peptide synthesis (hereinafter referred to as "Lys-ε([$^{19}$F]FB)").

Example 1

Here is an example of synthesis of peptide 1 to 6.

(1) Synthesis of Protected Peptide Resin of Peptide 4

Using the peptide synthesizer (Model 433A, Applied Biosystems, Inc.), the peptide and the protected peptide resin was synthesized by a solid-phase synthesis method as follows.

Using Fmoc-SAL resin (0.65 mol/g, 0.32 mmol scal) as the starting resin carrier, a peptide chain was successively extended according to the sequence, using, as raw materials, Fmoc-amino acid derivatives employed in a common Fmoc-peptide synthesis method. An Fmoc-amino acid derivative was set in the reaction vessel of the peptide synthesizer, and a solution of 1-[bisdimethylaminomethylene]-1H-benzotriazolium-3-oxido-hexafluorophosphate (HBTu) and 1-hydroxybenzotriazole (HOBt) as activators in dimethylformamide (DMF) was added to the reactor for reaction according to the software included with the synthesizer. The resulting resin was slowly stirred in piperidine-containing N-methylpyrrolidone to remove the Fmoc group, and the subsequent condensation of the amino acid derivative was conducted. As the amino acids each having a functional group in the side chain constituting the Fmoc amino acid derivatives used, tert-Butyl Tyr (hereinafter Tyr(OBu)) and Lys-ε([$^{19}$F]FB) were used. Amino acids were successively added according to the sequence to provide a protected peptide resin of H-Leu-Phe-Nle-Tyr-$_D$Lys-$_D$Lys-ε([$^{19}$F]FB)-SAL resin. Thereafter, formyl-Nle was condensed using DIC-HOOBt to construct a protected peptide resin having the sequence of interest.

(2) Deprotection and Cutting Out of Peptide 4 from Resin

The resulting protected peptide resin was treated at room temperature for 2 hours under TFA-TIS-H2O-(95/2.5/2.5, v/v) deprotection conditions for an ordinary method using trifluoroacetic acid to perform deprotection and cutting out of the peptide from the resin simultaneously. The carrier resin was filtered off from the reaction solution, followed by distilling off TFA. Ether was added to the residue, and the precipitate of the resulting crude product peptide was collected by filtration.

(3) Isolation and Purification of Peptide 4

The resulting crude product peptide was dissolved in acetonitrile and separated and purified in a water-acetonitrile ("acetonitrile" is hereinafter sometimes referred to as "MeCN") system containing 0.1% trifluoroacetic acid using the HPLC separation device LC-8A-1 (column: ODS 30×250 mm), manufactured by Shimadzu Corporation, to provide a peptide fraction of interest; acetonitrile was distilled off before making a lyophilized powder to provide the product of interest in the form of its trifluoroacetate.

To verify that the resulting peptide is the one of interest, EMI-MS and HPLC analyses were performed.

HPLC analysis conditions:
Column: YMC ODS-A (ODS, 150×4.6 mm I.D.)
Column Temperature: 40° C.
Eluants: Solution A: Water/0.1% TFA, Solution B: MeCN/0.1% TFA
Gradient: A/B: 90/10→40/60, 0→25 min linear
Flow Rate: 1.0 mL/min
Detector: 220 nm
Amount Injected: 1 μL
Sample Solution: 1 mg/200 μL DMSO
Analysis Results:
Retention Time: 22.1 min, Purity: 99.5%
m/z 1037.9 ([M+H]$^+$ 1074.3), m/z 537.7 ([M+2H]$^{2+}$ 537.7)
Molecular Weight: 1073.3

Other peptides were synthesized and identified in the similar way. Analysis conditions and results for each peptide are shown below.

Peptide 1
HPLC analysis conditions:
Column: YMC A-302 (ODS, 150×4.6 mm I.D.)
Column Temperature: 40° C.
Eluants: Solution A: Water/0.1% TFA, Solution B: MeCN/0.1% TFA
Gradient: A/B: 70/30→20/80, 0→25 min linear
Flow Rate: 1.0 mL/min
Detector: 220 nm
Amount Injected: 1 μL
Sample Solution: 1 mg/200 μL DMSO
Analysis Results:
Retention Time: 15.4 min, Purity: 95.2%
m/z 963.6 ([M+H]$^+$ 964.2)
Molecular Weight: 963.2

Peptide 2
HPLC analysis conditions:
Column: YMC A-302 (ODS, 150×4.6 mm I.D.)
Column Temperature: 40° C.
Eluants: Solution A: Water/0.1% TFA, Solution B: MeCN/0.1% TFA
Gradient: A/B: 70/30→20/80, 0→25 min linear
Flow Rate: 1.0 mL/min
Detector: 220 nm
Amount Injected: 1 μL
Sample Solution: 1 mg/200 μL DMSO
Analysis Results:
Retention Time: 17.1 min, Purity: 97.3%
m/z 945.6 ([M+H]$^+$ 946.1)
Molecular Weight: 945.1

Peptide 3
HPLC analysis conditions:
Column: YMC ODS-A (ODS, 150×4.6 mm I.D.)
Column Temperature: 40° C.
Eluants: Solution A: Water/0.1% TFA, Solution B: MeCN/0.1% TFA
Gradient: A/B: 90/10→40/60, 0→25 min linear
Flow Rate: 1.0 mL/min
Detector: 220 nm
Amount Injected: 1 μL
Sample Solution: 1 mg/200 μL 50% MeCN/H$_2$O
Analysis Results:
Retention Time: 20.7 min, Purity: 99.1%
m/z 1092.0 ([M+H]$^+$ 1092.3), m/z 546.6 ([M+2H]$^{2+}$ 546.7)
Molecular Weight: 1091.3

Peptide 5
HPLC analysis conditions:
Column: YMC ODS-A (ODS, 150×4.6 mm I.D.)

Column Temperature: 40° C.
Eluants: Solution A: Water/0.1% TFA, Solution B: MeCN/ 0.1% TFA
Gradient: A/B: 70/30→20/80, 0→25 min linear
Flow Rate: 1.0 mL/min
Detector: 220 nm
Amount Injected: 1 μL
Sample Solution: 1 mg/200 μL DMSO
Analysis Results:
Retention Time: 10.7 min, Purity: 97.4%
m/z 1091.9 ([M+H]$^+$ 1092.3), m/z 546.8 ([M+2H]$^{2+}$ 546.7)
Molecular Weight: 1091.3
Peptide 6
HPLC analysis conditions:
Column: YMC ODS-A (ODS, 150×4.6 mm I.D.)
Column Temperature: 40° C.
Eluants: Solution A: Water/0.1% TFA, Solution B: MeCN/ 0.1% TFA
Gradient: A/B: 90/10→40/60, 0→25 min linear
Flow Rate: 1.0 mL/min
Detector: 220 nm
Amount Injected: 1 μL
Sample Solution: 1 mg/200 μL DMSO
Analysis Results:
Retention Time: 20.1 min, Purity: 99.3%
m/z 601.6 ([M+H]$^+$ 601.7)
Molecular Weight: 1201.5
Peptide 7
HPLC analysis conditions:
Column: YMC ODS-A (ODS, 150×4.6 mm I.D.)
Column Temperature: 40° C.
Eluants: Solution A: Water/0.1% TFA, Solution B: MeCN/ 0.1% TFA
Gradient: A/B: 90/10→40/60, 0→25 min linear
Flow Rate: 1.0 mL/min
Detector: 220 nm
Amount Injected: 1 μL
Sample Solution: 1 mg/200 μL DMSO
Analysis Results:
Retention Time: 18.6 min, Purity: 99.8%
m/z 665.7 ([M+H]$^+$ 665.8), m/z 444.2 ([M+3H]$^{3+}$ 444.2)
Molecular Weight: 1329.7

Example 2

Binding Assay/Inhibition Assay: Evaluation of Binding Affinity for Formylated Peptide Receptor (FPR)

The compounds obtained in Example 1 and FMLP (fMLF) were evaluated for binding affinity for FPR by the following method.

Each peptide having a different concentration (DMSO solution, 10 μL), 2 nmol/L [$^{125}$I] Trp-Lys-Tyr-Met-Val-$_D$Met (10 μL) as radioligand, and FPR (10 μL) were added to a binding buffer (170 μL) and incubated at 25° C. for 1 hour, followed by collection by filtration (cell harvesters) using a GF/C filter coated with a polylysine buffer. After washing, radioactivity left on the filter was measured using a γ counter. [$^{125}$I] Trp-Lys-Tyr-Met-Val-$_D$Met means a positive control having affinity for FPR and was obtained from PerkinElmer Co., Ltd. for use.

*Binding buffer: 50 mmol/L Hepes, pH 7.4, 5 mmol/L MgCl$_2$, 1 mmol/L CaCl$_2$, 0.2% BSA Wash buffer: 50 mmol/L Hepes, pH 7.4, 500 mmol/L NaCl, 0.1% BSA Polylysine buffer: Poly-L-lysine hydrobromate 100 mg/wash buffer 100 mL The evaluation results are shown in Table 1.

Ki values in the table were calculated using the following equation (1).

[Equation 1]

$$Ki = \frac{IC_{50}}{1 + \frac{[L]}{K_d}} \quad (1)$$

IC$_{50}$: Calculation from Graph Pad
K$_d$: K$_d$ Value of Radioligand=0.39 nM
[L]: Concentration of Radioligand (Adjusted to 0.2 nM)

TABLE 1

| Compound | | Ki [nmol/L] (Mean value ± SD) |
|---|---|---|
| Peptides of present invention | Peptide 1 | 0.04 ± 0.04 |
| | Peptide 2 | 0.40 ± 0.36 |
| | Peptide 3 | 0.46 ± 0.07 |
| | Peptide 4 | 1.22 ± 0.40 |
| | Peptide 5 | 0.63 ± 0.14 |
| Control Peptides | Peptide 6 | 21.9 ± 12.7 |
| | Peptide 7 | 86.7 ± 33.8 |
| | FMLP | 4.25 ± 2.21 |

The results of Table 1 show that the compounds of the present invention exhibits a lower Ki value and has higher affinity for FPR, i.e., higher accumulation in an inflammation, than the compounds that are not according to the present invention.

Example 3

Synthesis of Formyl-Nle-Leu-Phe-Nle-Tyr-$_D$Lys-$_D$Lys-ϵ([$^{18}$F]FB)-NH$_2$

[Step 1] Synthesis of the Precursor for Radiolabeling
Precursor: formyl-Nle-Leu-Phe-Nle-Tyr-$_D$Lys (Fmoc)-$_D$Lys-NH$_2$ (1) Synthesis of Protected Peptide Resin Using the automated peptide synthesizer (Model 433A, Applied Biosystems, Inc.), the peptide was synthesized by a method which involves binding amino acids one by one from the carboxyl terminal sides according to the attached software (a solid-phase synthesis method). A protected peptide resin was synthesized. Using Fmoc-SAL resin (0.65 mol/g, 0.32 mmol scal) as the starting resin carrier, a peptide chain was successively extended according to the sequence, using, as raw materials, Fmoc-amino acid derivatives employed in a common Fmoc-peptide synthesis method. An Fmoc-amino acid derivative was set in the reaction vessel of the peptide synthesizer, and a solution of 1-[bisdimethylaminomethylene]-1H-benzotriazolium-3-oxido-hexafluorophosphate (HBTu) and 1-hydroxybenzotriazole (HOBt) as activators in dimethylformamide (DMF) was added to the reactor for reaction according to the software included with the synthesizer. The resulting resin was slowly stirred in piperidine-containing N-methylpyrrolidone to remove the Fmoc group, and the subsequent condensation of the amino acid derivative was conducted.

Tyr (OBu), Lys (Boc) and Lys (p-methyltrityl(hereinafter Mtt)) were used as the amino acids each having a functional group in the side chain constituting the Fmoc amino acid derivatives used. Amino acids were successively added according to the sequence to provide a protected peptide resin of H-Leu-Phe-Nle-Tyr(OBu)-$_D$Lys(Mtt)-$_D$Lys(Boc)-SAL resin. Thereafter, formyl-Nle was condensed using DIC-HOOBt to construct a protected peptide resin having the sequence of interest. Consequently, Mtt group is selectively deleted using TFA-TIS-DCM (1/5/94, v/v/v), followed Fmoc group is condensed into the amide group in the side chain of Lys using Fmoc-OSu to provide a protected peptide resin having the sequence of formyl-Nle-Leu-Phe$_7$Nle-Tyr (OBu)-$_D$ Lys (Fmoc)-$_D$Lys(BOC)-SAL Resin.

(2) Deprotection and Cutting Out from Resin

The resulting protected peptide resin was treated at room temperature for 2 hours under TFA-TIS-H$_2$O-(95/2.5/2.5, v/v) deprotection conditions for an ordinary method using trifluoroacetic acid to perform deprotection and cutting out of the peptide from the resin simultaneously. The carrier resin was filtered off from the reaction solution, followed by distilling off TFA. Ether was added to the residue, and the precipitate of the resulting crude product peptide was collected by filtration.

(3) Isolation and Purification of Peptide

The resulting crude product peptide was dissolved in acetonitrile and separated and purified in a water-acetonitrile system containing 0.1% trifluoroacetic acid using the HPLC separation device LC-8A-1 (column: ODS 30×250 mm), manufactured by Shimadzu Corporation, to provide a peptide fraction of interest; acetonitrile was distilled off before making a lyophilized powder to provide the product of interest in the form of its trifluoroacetate.

To verify that the resulting peptide is the one of interest, EMI-MS and HPLC analyses were performed.

HPLC analysis conditions:
Column: YMC A-302 (ODS, 150×4.6 mm I.D.)
Column Temperature: 40° C.
Eluants: Solution A: Water/0.1% TFA, Solution B: MeCN/0.1% TFA
Gradient: A/B: 70/30→20/80, 0→25 min linear
Flow Rate: 1.0 mL/min
Detector: 220 nm
Amount Injected: 1 µL
Sample Solution: 1 mg/200 µL 25% MeCN/H$_2$O
Analysis Results:
Retention Time: 17.0 min, Purity: 98.4%
m/z 1173.9 ([M+H]$^+$ 1174.4), m/z 587.6 ([M+2H]$^{2+}$ 587.7)
Molecular Weight: 1173.4

[Step 2] Synthesis of Radioactive Halogen-Containing Monomer

1. Kryptofix 222 (trade name, manufactured by Merck Ltd.) (10 mg) was dissolved in dehydrated acetonitrile (500 µL) in a light-shielded vial (hereinafter referred to as a "reaction vial"), to which a K$_2$CO$_3$ aqueous solution of $^{18}$F$^-$ (100 to 500 µL) (amount of radioactivity: 18.5 GBq) was then added before stirring.

2. The vial was heated in a 110° C. oil bath while blowing nitrogen gas thereinto until the solvent evaporated (estimated time: 10 min). In addition, the solvent was driven off by adding dehydrated acetonitrile (400 µL×3, estimated time: 3 min for each addition), and water was completely driven off.

3. t-Butyl 4-N,N,N-trimethyl-ammoniumbenzoate triflate (0.5 mg) was dissolved in dehydrated acetonitrile (1 mL), which was then added to the reaction vial before vigorously stirring for reaction at 90° C. for 10 min.

4. After reaction, tetrapropylammonium hydroxide (1 mol/L in H$_2$O, 20 µL) was added thereto before stirring for reaction at 120° C. for 5 min.

5. After reaction, TSTU (15 mg) was dissolved in (dehydrated) acetonitrile (100 µL), which was then added to the reaction vial before stirring for reaction at 90° C. for 2 min.

6. The reaction solution was diluted with a 5% acetic acid aqueous solution (10 mL) and then passed through Sep-Pak (trademark, manufactured by Nihon Waters K.K.) plus PS-2 activated with (5 mL each of) acetonitrile and water; the column was washed with water/acetonitrile (80/20, 20 mL) and [$^{18}$F]SFB was eluted using acetonitrile (2.5 mL).

[Step 3] Labeling of Peptide with Radioactive Fluorine 0.3 mg of the peptide as the labeled precursor was dissolved in 40 µL of acetonitrile (MeCN) and 40 µL of a borate buffer, which was then added to [$^{18}$F]SFB concentrated in a stream of Ar at 70° C. The resulting mixture was adjusted to a pH of 8.5 to 9.0 with MeCN/Et$_3$N=98/2 for reaction for 1 hour and 30 minutes.

After reaction, the deprotection reaction of Fmoc was performed. Piperidine was added thereto to make a solution having a concentration of 20%, which was then reacted for 15 to 30 minutes to complete the deprotection reaction of Fmoc.

Separation was performed using HPLC, followed by purity determination.

HPLC analysis conditions:
Column: Cosmosil (5C18-ARII, 250×10 mm I.D.)
Column Temperature: 30° C.
Eluants: Solution A: Water/0.1% TFA, Solution B: MeCN/0.1% TFA
Gradient: A/B: 55/45→25/75, 0→30 min linear
Flow Rate: 2.0 mL/min
Detector: 220 nm
Amount Injected: 25 µL
Analysis Results:
Retention Time: 11.1 min, Radiochemical Yield: 18%, Radiochemical Purity: 99% or more Example 4

Synthesis of Formyl-Met-Leu-Phe-Nle-Tyr-$_D$Lys-ε ([$^{18}$F]FB)-$_D$Lys-NH$_2$

[Step 1] Synthesis of the Precursor for Radiolabeling

Precursor: formyl-Met-Leu-Phe-Nle-Tyr-$_D$Lys-$_D$Lys (Fmoc)-NH$_2$ (1) Synthesis of Protected Peptide Resin Using the automated peptide synthesizer (Model 433A, Applied Biosystems, Inc.), the peptide was synthesized by a method which involves binding amino acids one by one from the carboxyl terminal sides according to the included software (a solid-phase synthesis method). A protected peptide resin was synthesized. Using Fmoc-SAL resin (0.65 mol/g, 0.32 mmol scal) as the starting resin carrier, a peptide chain was successively extended according to the sequence, using, as raw materials, Fmoc-amino acid derivatives employed in a common Fmoc-peptide synthesis method. An Fmoc-amino acid derivative was set in the reaction vessel of the peptide synthesizer, and a solution of 1-[bisdimethylaminomethylene]-1H-benzotriazolium-3-oxido-hexafluorophosphate (HBTu) and 1-hydroxybenzotriazole (HOBt) as activators in dimethylformamide (DMF) was added to the reactor for reaction according to the software included with the synthesizer. The resulting resin was slowly stirred in piperidine-containing N-methylpyrrolidone to remove the Fmoc group, and the subsequent condensation of the amino acid derivative was conducted.

As the amino acids each having a functional group in the side chain constituting the Fmoc amino acid derivatives used, Tyr (OBu), Lys (Boc) and Lys (Mtt) were used. Amino acids were successively added according to the sequence to provide a protected peptide resin of H-Leu-Phe-Nle-Tyr(OBu)-$_D$Lys(Boc)-$_D$Lys(Mtt)-SAL resin. Thereafter, formyl-Met was condensed using DIC-HOOBt to construct a protected peptide resin having the sequence of interest. Consequently, Mtt group is selectively deleted using TFA-TIS-DCM (1/5/94, v/v), followed Fmoc group is condensed into the amide group in the side chain of Lys using Fmoc-OSu to provide a protected peptide resin having the sequence of formyl-Met-Leu-Phe-Nle-Tyr(OBu)-$_D$Lys(Boc)-$_D$Lys(Fmoc)-SAL Resin.

(2) Deprotection and Cutting Out from Resin

The resulting protected peptide resin was treated at room temperature for 2 hours under TFA-TIS-H$_2$O-(95/2.5/2.5, v/v) deprotection conditions for an ordinary method using trifluoroacetic acid to perform deprotection and cutting out of the peptide from the resin simultaneously. The carrier resin was filtered off from the reaction solution, followed by distilling off TFA. Ether was added to the residue, and the precipitate of the resulting crude product peptide was collected by filtration.

(3) Isolation and Purification of Peptide

The resulting crude product peptide was dissolved in acetonitrile and separated and purified in a water-acetonitrile system containing 0.1% trifluoroacetic acid using the HPLC separation device LC-8A-1 (column: ODS 30×250 mm), manufactured by Shimadzu Corporation, to provide a peptide fraction of interest; acetonitrile was distilled off before making a lyophilized powder to provide the product of interest in the form of its trifluoroacetate.

To verify that the resulting peptide is the one of interest, EMI-MS and HPLC analyses were performed.

HPLC analysis conditions:
Column: YMC A-302 (ODS, 150×4.6 mm I.D.)
Column Temperature: 40° C.
Eluants: Solution A: Water/0.1% TFA, Solution B: MeCN/0.1% TFA
Gradient: A/B: 70/30→20/80, 0→25 min linear
Flow Rate: 1.0 mL/min
Detector: 220 nm
Amount Injected: 1 µL
Sample Solution: 1 mg/200 µL 25% MeCN/H$_2$O
Analysis Results:
Retention Time: 15.6 min, Purity: 96.7%
m/z 1191.9 ([M+H]$^+$ 1192.5), m/z 596.7 ([M+2H]$^{2+}$ 596.7)
Molecular Weight: 1191.5

[Step 2] Synthesis of Radioactive Halogen-Containing Monomer

1. Kryptofix 222 (trade name, manufactured by Merck Ltd.) (10 mg) was dissolved in dehydrated acetonitrile (500 µL) in a light-shielded vial (hereinafter referred to as a "reaction vial"), to which a K$_2$CO$_3$ aqueous solution of $^{18}$F$^-$ (100 to 500 µL) (amount of radioactivity: 7.46 GBq) was then added before stirring.

2. The vial was heated in a 110° C. oil bath while blowing nitrogen gas thereinto until the solvent evaporated (estimated time: 10 min). In addition, the solvent was driven off by adding dehydrated acetonitrile (400 µL×3, estimated time: 3 min for each addition), and water was completely driven off.

3. t-Butyl 4-N,N,N-trimethyl-ammoniumbenzoate triflate (0.5 mg) was dissolved in dehydrated acetonitrile (1 mL), which was then added to the reaction vial before vigorously stirring for reaction at 90° C. for 10 min.

4. After reaction, tetrapropylammonium hydroxide (1 mol/L in H$_2$O, 20 µL) was added thereto before stirring for reaction at 120° C. for 5 min.

5. After reaction, TSTU (15 mg) was dissolved in (dehydrated) acetonitrile (100 µL), which was then added to the reaction vial before stirring for reaction at 90° C. for 2 min.

6. The reaction solution was diluted with a 5% acetic acid aqueous solution (10 mL) and then passed through Sep-Pak (trademark, manufactured by Nihon Waters K.K.) plus PS-2 activated with (5 mL each of) acetonitrile and water; the column was washed with water/acetonitrile (80/20, 20 mL) and [$^{18}$F]SFB was eluted using acetonitrile (2.5 mL).

[Step 3] Labeling of Peptide with Radioactive Fluorine 0.3 mg of the peptide as the labeled precursor was dissolved in 40 µL of acetonitrile (MeCN) and 40 µL of a borate buffer, which was then added to [$^{18}$F]SFB concentrated in a stream of Ar at 70° C. The resulting mixture was adjusted to a pH of 8.5 to 9.0 with MeCN/Et$_3$N=98/2 for reaction for 1 hour and 30 minutes. After reaction, the deprotection reaction of Fmoc was performed. Piperidine was added thereto to make a solution having a concentration of 20%, which was then reacted for 15 to 30 minutes to complete the deprotection reaction of Fmoc. Separation was performed using HPLC, followed by purity determination.

HPLC analysis conditions:
Column: Cosmosil (5C18-ARII, 250×10 mm I.D.)
Column Temperature: 30° C.
Eluants: Solution A: Water/0.1% TFA, Solution B: MeCN/0.1% TFA
Gradient: A/B: 55/45→25/75, 0→30 min linear
Flow Rate: 2.0 mL/min
Detector: 220 nm
Amount Injected: 25 µL
Analysis Results:
Retention Time: 9.6 min, Radiochemical Yield: 3%, Radiochemical Purity: 99% or More, Yield: 11.1 MBq Example 5

Synthesis of Formyl-Met-Leu-Phe-Nle-Tyr-$_D$Lys-$_D$Lys-ε([$^{18}$F]FB)-$_D$Lys-NH$_2$

[Step 1] Synthesis of the Precursor for Radiolabeling

Precursor: formyl-Met-Leu-Phe-Nle-Tyr-$_D$Lys(Fmoc)-$_D$Lys-NH$_2$ (1) Synthesis of Protected Peptide Resin Using the automated peptide synthesizer (Model 433A, Applied Biosystems, Inc.), the peptide was synthesized by a method which involves binding amino acids one by one from the carboxyl terminal sides according to the included software (a solid-phase synthesis method). A protected peptide resin was synthesized. Using Fmoc-SAL resin (0.65 mol/g, 0.32 mmol scal) as the starting resin carrier, a peptide chain was successively extended according to the sequence, using, as raw materials, Fmoc-amino acid derivatives employed in a common Fmoc-peptide synthesis method. An Fmoc-amino acid derivative was set in the reaction vessel of the peptide synthesizer, and a solution of 1-[bisdimethylaminomethylene]-1H-benzotriazolium-3-oxido-hexafluorophosphate (HBTu) and 1-hydroxybenzotriazole (HOBt) as activators in dimethylformamide (DMF) was added to the reactor for reaction according to the software included with the synthesizer. The resulting resin was slowly stirred in piperidine-containing N-methylpyrrolidone to remove the Fmoc group, and the subsequent condensation of the amino acid derivative was conducted.

As the amino acids each having a functional group in the side chain constituting the Fmoc amino acid derivatives used, Tyr (OBu), Lys (Boc) and Lys (Mtt) were used. Amino acids were successively added according to the sequence to provide a protected peptide resin of H-Leu-Phe-Nle-Tyr(OBu)-$_D$Lys(Mtt)-$_D$Lys(Boc)-SAL resin. Thereafter, formyl-Met was condensed using DIC-HOOBt to construct a protected peptide resin having the sequence of interest. Consequently, Mtt group is selectively deleted using TFA-TIS-DCM (1/5/94, v/v), followed Fmoc group is condensed into the amide group in the side chain of Lys using Fmoc-OSu to provide a protected peptide resin having the sequence of formyl-Met-Leu-Phe-Nle-Tyr(OBu)-$_D$Lys(Fmoc)-$_D$Lys(BOC)-SAL Resin.

(2) Deprotection and Cutting Out from Resin

The resulting protected peptide resin was treated at room temperature for 2 hours under TFA-TIS-H$_2$O-(95/2.5/2.5, v/v) deprotection conditions for an ordinary method using trifluoroacetic acid to perform deprotection and cutting out of the peptide from the resin simultaneously. The carrier resin was filtered off from the reaction solution, followed by distilling off TFA. Ether was added to the residue, and the precipitate of the resulting crude product peptide was collected by filtration.

(3) Isolation and Purification of Peptide

The resulting crude product peptide was dissolved in acetonitrile and separated and purified in a water-acetonitrile system containing 0.1% trifluoroacetic acid using the HPLC separation device LC-8A-1 (column: ODS 30×250 mm), manufactured by Shimadzu Corporation, to provide a peptide fraction of interest; acetonitrile was distilled off before making a lyophilized powder to provide the product of interest in the form of its trifluoroacetate.

To verify that the resulting peptide is the one of interest, EMI-MS and HPLC analyses were performed.

HPLC analysis conditions:
Column: YMC ODS-A (ODS, 150×4.6 mm I.D.)
Column Temperature: 40° C.
Eluants: Solution A: Water/0.1% TFA, Solution B: MeCN/0.1% TFA
Gradient: A/B: 70/30→20/80, 0→25 min linear
Flow Rate: 1.0 mL/min
Detector: 220 nm
Amount Injected: 1 µL
Sample Solution: 1 mg/200 µL 50% MeCN/H2O
Analysis Results:
Retention Time: 15.5 min, Purity: 98.0%
m/z 1191.9 ([M+H]$^+$ 1192.5), m/z 597.0 ([M+2H]$^{2+}$ 596.7)
Molecular Weight: 1191.5

[Step 2] Synthesis of Radioactive Halogen-Containing Monomer

1. Kryptofix 222 (trade name, manufactured by Merck Ltd.) (10 mg) was dissolved in dehydrated acetonitrile (500 µL) in a light-shielded vial (hereinafter referred to as a "reaction vial"), to which a K2CO3 aqueous solution of $^{18}$F$^-$ (100 to 500 µL) (amount of radioactivity: 7.46 GBq) was then added before stirring.

2. The vial was heated in a 110° C. oil bath while blowing nitrogen gas thereinto until the solvent evaporated (estimated time: 10 min). In addition, the solvent was driven off by adding dehydrated acetonitrile (400 µL×3, estimated time: 3 min for each addition), and water was completely driven off.

3. t-Butyl 4-N,N,N-trimethyl-ammoniumbenzoate triflate (0.5 mg) was dissolved in dehydrated acetonitrile (1 mL), which was then added to the reaction vial before vigorously stirring for reaction at 90° C. for 10 min.

4. After reaction, tetrapropylammonium hydroxide (1 mol/L in H$_2$O, 20 µL) was added thereto before stirring for reaction at 120° C. for 5 min.

5. After reaction, TSTU (15 mg) was dissolved in (dehydrated) acetonitrile (100 µL), which was then added to the reaction vial before stirring for reaction at 90° C. for 2 min.

6. The reaction solution was diluted with a 5% acetic acid aqueous solution (10 mL) and then passed through Sep-Pak (trademark, manufactured by Nihon Waters K.K.) plus PS-2 activated with (5 mL each of) acetonitrile and water; the column was washed with water/acetonitrile (80/20, 20 mL) and [$^{18}$F]SFB was eluted using acetonitrile (2.5 mL).

[Step 3] Labeling of Peptide with Radioactive Fluorine 0.3 mg of the peptide as the labeled precursor was dissolved in 40 mL of acetonitrile (MeCN) and 40 µL of a borate buffer, which was then added to [$^{18}$F]SFB concentrated in a stream of Ar at 70° C. The resulting mixture was adjusted to a pH of 8.5 to 9.0 with MeCN/Et$_3$N=98/2 for reaction for 1 hour and 30 minutes. After reaction, the deprotection reaction of Fmoc was performed. Piperidine was added thereto to make a solution having a concentration of 20%, which was then reacted for 15 to 30 minutes to complete the deprotection reaction of Fmoc. Separation was performed using HPLC, followed by purity determination.

HPLC analysis conditions:
Column: Cosmosil (5C18-ARII, 250×10 mm I.D.)
Column Temperature: 30° C.
Eluants: Solution A: Water/0.1% TFA, Solution B: MeCN/0.1% TFA
Gradient: A/B: 60/40→25/75, 0→25 min linear
Flow Rate: 2.0 mL/min
Detector: 220 nm
Amount Injected: 10 µL
Analysis Results:
Retention Time: 16.7 min, Radiochemical Yield: 13%, Radiochemical Purity: 97% or More Example 6

For the compounds obtained in Examples 3, 4 and 5, PET imaging was performed as follows.

Each concentrated labeled solution was diluted with saline and administered to inflammation model mice subjected to inhalation anesthesia using isoflurane; Dynamic PET imaging was performed for 60 minutes immediately after administration.

Mouse 1 for Example 3: 156 µCi/50 µL
Mouse 2 for Example 4: 18 µCi/100 µL
Mouse 3 for Example 5: 580 µCi/120 µL Preparation of Inflammation Model Overnight cultured *Escherichia coli* (XL1Blue) was centrifuged, and the collected pellet was suspended in saline. The suspension was centrifuged again, and the resulting pellet was inoculated into the right femoral region muscle of the mice (ddY, male, 6 weeks old) under inhalation anesthesia. These mice were used for PET imaging after 4 days.

Figure 3:
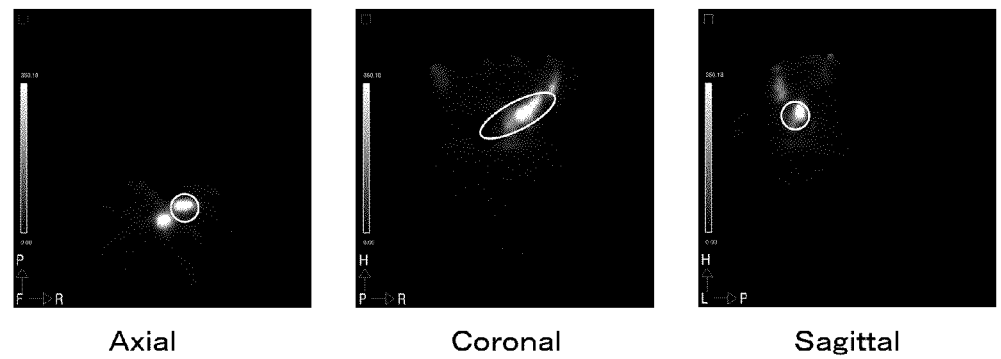
FIG. 3 shows the image of F-18-peptide of formyl-Nle-Leu-Phe-Nle-Tyr-$_D$Lys-$_D$Lys-ϵ([$^{18}$F]FB)-NH$_2$ obtained in Example 3.
Figure 4:
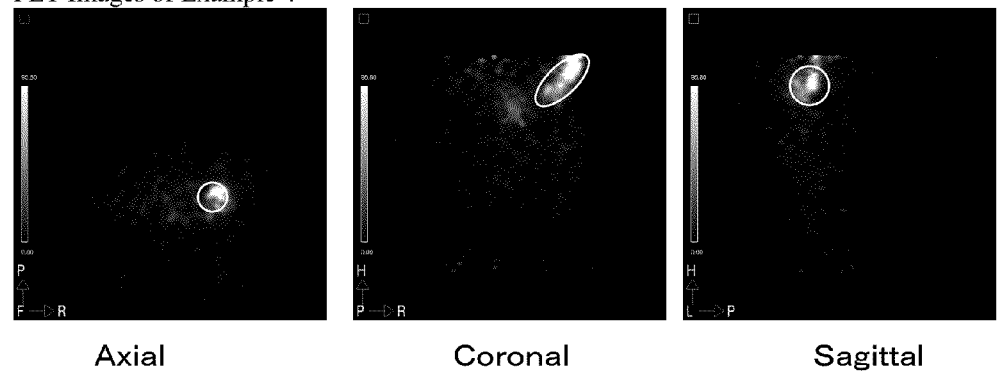
FIG. 4 shows the image of F-18 peptide of formyl-Met-Leu-Phe-Nle-Tyr-$_D$Lys-ϵ([$^{18}$F]FB)-$_D$Lys-NH$_2$; obtained in Example 4.
Figure 5:
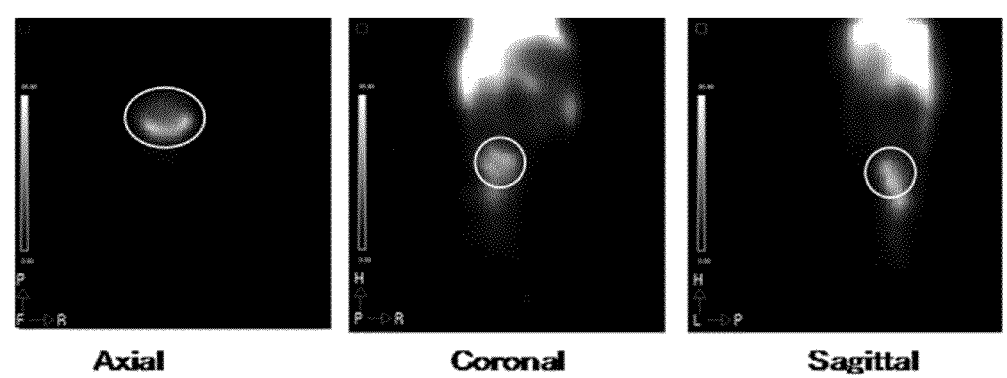
FIG. 5 shows the image of F-18 peptide of formyl-Met-Leu-Phe-Nle-Tyr-$_D$Lys-$_D$Lys-ϵ([$^{18}$F]FB)-NH$_2$; obtained in Example 5

PET images of Mouse 1, 2 and 3 at 45 minutes after administration are shown in FIGS. 3, 4 and 5, respectively. In the figures, the circles indicate inflammatory sites.

The results show the following.

Accumulation in the inflamed sites was observed early after administration, and the accumulation increased with the lapse of time.

Embodiments of the present invention relate to a compound accumulating in an inflammatory site, a diagnostic agent containing the compound in a labeled state and its precursor compound for labeling. More in detail, embodiments of the present invention relate to a novel compound having radioactive halogen and properties of accumulation specific to the inflammatory site in vivo in association with a seat of disease including a diabetic foot. Also, embodiments of the present invention relate to a diagnostic agent containing said compound in a labeled state as the active ingredient, which is useful for radioisotope diagnosis and its precursor compound for labeling.

What is claimed:

1. A compound accumulating in inflammatory site represented by a following formula (1):

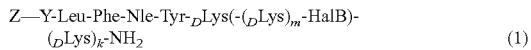

wherein, in the formula (1),

Z represents a protective group for an amino group, which is acyl group having 1 to 9 carbon atoms, acyloxy groups having 2 to 9 carbon atoms, lower alkyl groups having 1 to 6 carbon atoms, or carbamyl groups;

Y represents Met or Nle;

m represents 1 or 0;

k represents 1 or 0; and

HalB represents a substituted benzoic acid having a radioactive halogen in its aromatic ring.

2. The compound according to claim 1, wherein Z in the formula (1) is a formyl group.

3. The compound according to claim 1, wherein said radioactive halogen in HalB is $^{121}$I.

4. The compound according to claim 1, wherein said radioactive halogen in HalB is $^{123}$I.

5. The compound according to claim 1, wherein said radioactive halogen in HalB is $^{125}$I.

6. The compound according to claim 1, wherein said radioactive halogen in HalB is $^{131}$I.

7. The compound according to claim 1, wherein said radioactive halogen in HalB is $^{124}$I.

8. The compound according to claim 1, wherein the said radioactive halogen in HalB is $^{18}$F (HalB in this case is represented by [$^{18}$F]FB where FB is fluorobenzoyl.

9. The compound according to claim 1, wherein said compound represented by the formula (1) is formyl-Met-Leu-Phe-Nle-Tyr-$_D$Lys-ε([$^{18}$F]FB)-NH$_2$ where FB is fluorobenzoyl.

10. The compound according to claim 1, wherein said compound represented by the formula (1) is formyl-Met-Leu-Phe-Nle-Tyr-$_D$Lys-$_D$Lys-ε([$^{18}$F]FB)-NH$_2$ where FB is fluorobenzoyl.

11. The compound according to claim 1, wherein said compound represented by the formula (1) is formyl-Nle-Leu-Phe-Nle-Tyr-$_D$Lys-ε([$^{18}$F]FB)-NH$_2$ where FB is fluorobenzoyl.

12. The compound according to claim 1, wherein said compound represented by the formula (1) is formyl-Nle-Leu-Phe-Nle-Tyr-$_D$Lys-$_D$Lys-ε([$^{18}$F]FB)-NH$_2$ where FB is fluorobenzoyl.

13. The compound according to claim 1, wherein said compound represented by the formula (1) is formyl-Nle-Leu-Phe-Nle-Tyr-$_D$Lys-ε([$^{18}$F]FB)-$_D$Lys-NH$_2$ where FB is fluorobenzoyl.

14. The compound according to claim 1, wherein said compound represented by the formula (1) is formyl-Met-Leu-Phe-Nle-Tyr-$_D$Lys-ε([$^{18}$F]FB)-$_D$Lys-NH$_2$ where FB is fluorobenzoyl.

15. A diagnostic agent for imaging an inflammatory site, comprising a radioactive compound as an active ingredient, the compound being represented by the following formula (1):

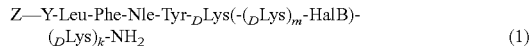

wherein, in the formula (1),

Z represents a protective group for an amino group, which is acyl group having 1 to 9 carbon atoms, acyloxy groups having 2 to 9 carbon atoms, lower alkyl groups having 1 to 6 carbon atoms, or carbamyl groups;

Y represents Met or Nle;

m represents 1 or 0;

k represents 1 or 0; and

HalB represents a substituted benzoic acid having a radioactive halogen in its aromatic ring.

16. The compound according to claim 15, wherein Z in the formula (1) is a formyl group.

17. A diagnostic agent for imaging an inflammatory site from a diabetic foot, comprising a compound being represented by the following formula (1):

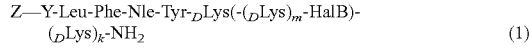

wherein, in the formula (1),

Z represents a protective group for an amino group, which is acyl group having 1 to 9 carbon atoms, acyloxy groups having 2 to 9 carbon atoms, lower alkyl groups having 1 to 6 carbon atoms, or carbamyl groups;

Y represents Met or Nle;

m represents 1 or 0;

k represents 1 or 0; and

HalB represents a substituted benzoic acid having a radioactive halogen in its aromatic ring.

* * * * *